United States Patent
Cozzi et al.

(10) Patent No.: US 6,596,845 B1
(45) Date of Patent: Jul. 22, 2003

(54) CINNAMOYL DISTAMYCIN ANALOGOUS DERIVATIVES, PROCESS FOR THEIR PREPARATION, AND THEIR USE AS ANTITUMOR AGENTS

(75) Inventors: Paolo Cozzi, Milan (IT); Pier Giovanni Baraldi, Ferrara (IT); Italo Beria, Villamarzana (IT); Marina Caldarelli, Milan (IT); Maria Cristina Geroni, Milan (IT); Giulia Pennella, Milan (IT); Romeo Romagnoli, Milan (IT)

(73) Assignee: Pharmacia Italia S.p.A., Milan (IT)

( * ) Notice: Subject to any disclaimer, the term of this patent is extended or adjusted under 35 U.S.C. 154(b) by 0 days.

(21) Appl. No.: 09/701,557

(22) PCT Filed: May 22, 1999

(86) PCT No.: PCT/EP99/03595

§ 371 (c)(1),
(2), (4) Date: Dec. 4, 2000

(87) PCT Pub. No.: WO99/64413

PCT Pub. Date: Dec. 16, 1999

(30) Foreign Application Priority Data

Jun. 5, 1998 (GB) .............................................. 9812211

(51) Int. Cl.$^7$ ................................................. C07K 5/08
(52) U.S. Cl. ........................ 530/331; 530/330; 514/18; 514/19
(58) Field of Search ................................ 530/330, 331; 514/17–19

(56) References Cited

FOREIGN PATENT DOCUMENTS

WO    96 05196    2/1996
WO    97 43258    11/1997

OTHER PUBLICATIONS

Cozzi et al., "Novel phenyl nitrogen mustard and half–mustard derivatives of distamycin A" Bioorg. Med. Chem. Lett. (1997), 7(23), 2985–2990.

Cozzi et al., "Novel phenyl nitrogen mustard and half–mustard derivatives of amidino–modified distamycin", Bioorg. Med. Chem. Lett. (1997), 7(23) 2979–2984.

Primary Examiner—Christopher S. F. Low
Assistant Examiner—David Lukton
(74) Attorney, Agent, or Firm—Arent Fox Kintner Plotkin & Kahn

(57) ABSTRACT

Compounds which are cinnamoyl distamycin derivatives of formula (I), wherein n is 2, 3, or 4; $R_0$ is $C_1$–$C_4$ alkyl or $C_1$–$C_3$ haloalkyl; $R_1$ and $R_2$, which are the same or different, are selected from hydrogen, $C_1$–$C_4$ alkyl optionally substituted by one or more fluorine atoms; and $C_1$–$C_4$ alkoxy; X is a halogen atom; Y and Z are the same or different and are selected, independently for each heterocyclic ring of the polyheterocyclic chain, from N and CH; B is selected from (a), (b), (c), (d), (e), (f), (g) and (h) wherein $R_3$, $R_4$, $R_5$, $R_6$ and $R_7$ are, independently from each other, hydrogen or $C_1$–$C_4$ alkyl; or pharmaceutically acceptable salts thereof; provided that at least one of the heterocyclic rings within the polyheterocyclic chain is other than pyrrole; are useful as antitumor agents.

14 Claims, No Drawings

CINNAMOYL DISTAMYCIN ANALOGOUS DERIVATIVES, PROCESS FOR THEIR PREPARATION, AND THEIR USE AS ANTITUMOR AGENTS

The present invention relates to new alkylating antitumor agents analogous to Distamycin A, to a process for their preparation, to pharmaceutical compositions containing them and to their use as therapeutic agents. Distamycin A, whose formula is reported below

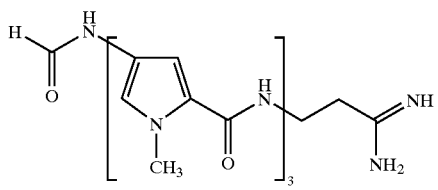

belongs to the family of the pyrroleamidine antibiotics and it is reported to interact reversibly and selectively with DNA-AT sequences, thus interfering with both replication and transcription. See, for a reference, Nature, 203, 1064 (1964); FEBS Letters, 7 (1970) 90; Prog. Nucleic Acids Res. Mol. Biol., 15, 285 (1975).

Several analogous to distamycin are known in the art.

DE-A-1795539 discloses distamycin derivatives in which the formyl group is replaced by a hydrogen atom or by the carboxylic acid residue of a $C_1$–$C_4$ aliphatic or cyclopentylpropionic acid.

EP-A-246,868 describes distamycin analogues in which the distamycin formyl group is substituted by aromatic, alicyclic or heterocyclic moieties bearing alkylating groups.

WO 97/28123 describes distamycin analogues in which the distamycin formyl group is substituted by an aromatic moiety bearing alkylating groups and the amidino group is replaced with different nitrogen-containing ending moieties.

WO 97/43258 discloses cinnamoyl distamycin derivatives amidino-modified as above reported.

Distamycin derivatives wherein at least one pyrrole ring of the polypyrrole framework is substituted by an imidazole or pyrazole ring are also reported in the literature; see, for a reference, Anti-Cancer Drug Design 8, 173–192 (1993); J. Am. Chem. Soc. Vol. 114, 5911–5919 (1992); Anti-Cancer Drug Design 6, 501–517 (1991); patent applications EP-A-0246868 and WO 96/05196.

It has now been found that a new class of distamycin derivatives as defined hereinunder, wherein at least one ring of the polypyrrole framework is other than pyrrole, the formyl group is substituted by a cinnamoyl moiety and the amidino group is optionally substituted by different nitrogen-containing ending groups, shows valuable biological properties.

Therefore, the present invention provides compounds which are cinnamoyl distamycin derivatives of formula:

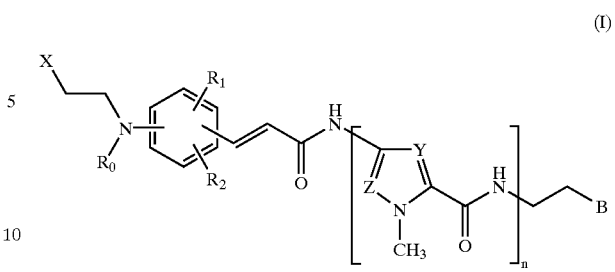

wherein:
n is 2, 3 or 4;
$R_0$ is $C_1$–$C_4$ alkyl or $C_1$–$C_3$ haloalkyl;
$R_1$ and $R_2$, which are the same or different, are selected from hydrogen, $C_1$–$C_4$ alkyl optionally substituted by one or more fluorine atoms; and $C_1$–$C_4$ alkoxy;
X is a halogen atom;
Y and Z are the same or different and are selected, independently for each heterocyclic ring of the polyheterocyclic chain, from N and CH;
B is selected from:

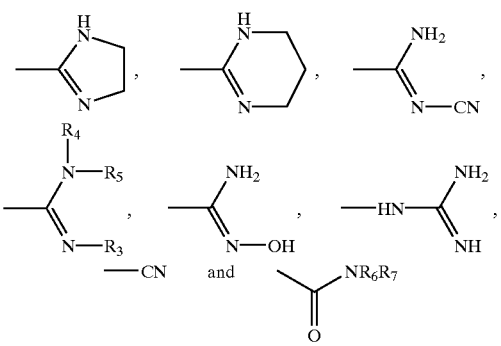

wherein $R_3$, $R_4$, $R_5$, $R_6$, and $R_7$ are, independently from each other, hydrogen or $C_1$–$C_4$ alkyl;
or pharmaceutically acceptable salts thereof;
provided that at least one of the heterocyclic rings within the polyheterocyclic chain is other than pyrrole.

The present invention includes within its scope also all the possible isomers covered by the compounds of formula (I), both separately and in admixture, as well as the metabolites and the pharmaceutically acceptable bio-precursors (otherwise known as pro-drugs) of the compounds of formula (I).

In the present description, unless otherwise specified, both terms alkyl and alkoxy include straight or branched $C_1$–$C_4$ alkyl and alkoxy groups such as, for instance, methyl, ethyl, n-propyl, isopropyl, n-butyl, isobutyl, sec-butyl, tert-butyl, methoxy, ethoxy, n-propoxy, isopropoxy, n-butoxy, isobutoxy, sec-butoxy and tert-butoxy.

Preferred $C_1$–$C_4$ alkyl or alkoxy groups are methyl, ethyl, methoxy and ethoxy groups.

When substituted by one or more fluorine atoms, the $C_1$–$C_4$ alkyl groups are preferably $C_1$–$C_4$ perfluoroalkyl groups, e.g. trifluoromethyl.

The term halogen atom includes fluorine, chlorine, bromine and iodine, being chlorine and bromine preferred.

As above reported, Y and Z are selected, independently for each heterocyclic ring of the polyheterocyclic chain, between N and CH. This means that within the compounds of formula (I) and for different heterocyclic rings Y can be either N as well as CH; the same applies for Z provided
that at least for one of the heterocyclic rings, Y and Z are not both CH.

Examples of the said heterocycles are pyrrole, pyrazole and imidazole.

Within the cinnamoyl derivatives of formula (I) the N,N-disubstituted amino group onto phenyl ring is in ortho, meta or para position; preferably, it is in meta or para position.

As to the $R_1$ and $R_2$ groups, they can be in any of the free positions of the phenyl ring.

Pharmaceutically acceptable salts of the compounds of formula (I) are their salts with pharmaceutically acceptable either inorganic or organic acids such as, for instance, hydrochloric, hydrobromic, sulfuric, nitric, acetic, propionic, succinic, malonic, citric, tartaric, methanesulfonic and p-toluenesulfonic acid.

A preferred class of compounds of the present invention is that wherein, in formula (I):

n is 3;

$R_0$ is ethyl or 2-chloroethyl;

$R_1$ and $R_2$ which are the same or different, are selected from hydrogen, methyl, methoxy or trifluoromethyl;

X is chloro;

Y and Z are the same or different and are selected, independently for each heterocyclic ring of the polyheterocyclic chain, from N and CH;

B is selected from:

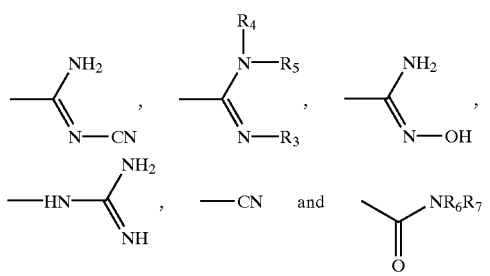

wherein $R_3$, $R_4$, $R_5$, $R_6$, and $R_7$ are, independently from each other, hydrogen or methyl;

or the pharmaceutically acceptable salts thereof;

provided that at least one of the heterocyclic rings within the polyheterocyclic chain is other than pyrrole.

Examples of specific compounds according to the present invention, especially in the form of salts, preferably with hydrochloric acid, are the following:

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamidine;

3-[1-methyl-3[1-methyl-3[1-methyl-4[4-N-ethyl-N-(2-chloroethyl)aminocinnamoylamido]pyrrole-2-carboxamido]pyrazole-5-carboxamido]pyrazole-5-carboxamido]propionamidine;

3-[1-methyl-3[1-methyl-3[1-methyl-4[3-N,N-bis(2-chloroethyl)aminocinnamoylamido]pyrrole-2-carboxamido]pyrazole-5-carboxamido]pyrazole-5-carboxamido]propionamidine;

3-[1-methyl-3[1-methyl-3[1-methyl-4[3-methyl-4-N,N-bis(2-chloroethyl)aminocinnamoyl]pyrrole-2-carboxamido]pyrazole-5-carboxamido]pyrazole-5-carboxamido]propionamidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionamidine;

3-[1-methyl-3[1-methyl-4[1-methyl-4[4-N-ethyl-N(2-chloroethyl)aminocinnamoylamido]pyrrole-2-carboxamido]pyrrole-2-carboxamido]pyrazole-5-carboxamido]propionamidine;

3-[1-methyl-4[1-methyl-4[1-methyl-4 [4-N,N-bis(2-chloroethyl)aminocinnamoylamido]pyrrole-2-carboxamido]pyrrole-2-carboxamido]imidazole-2-carboxamido]propionamidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamidine;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionamidine;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propioncyanamidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propioncyanamidine;

3-[1-methyl-4[1-methyl-4[1-methyl-4[4-N,N-bis(2-chloroethyl)aminocinnamoylamido]pyrrole-2-carboxamido2pyrrole-2-carboxamido]imidazole-2-carboxamido]propioncyanamidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propioncyanamidine;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propioncyanamidine;

3-[1-methyl-4[1-methyl-4[1-methyl-4[4-N-ethyl-N(2-chloroethyl)aminocinnamoylamido]pyrrole-2-carboxamido]pyrrole-2-carboxamido]imidazole-2-carboxamido]propioncyanamidine;

3-[1-methyl-4[1-methyl-3[1-methyl-4[4-N-ethylN(2-chloroethyl)aminocinnamoylamido]pyrrole-2-carboxamido]pyrazole-5-carboxamido]imidazole-2-carboxamido]propioncyanamidine;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamidoxime;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionamidoxime;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamidoxime;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamidoxime;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionamidoxime;

3-[-1-methyl-3[1-methyl-3[1-methyl-4[4-N-ethyl-N(2-chloroethyl)aminocinnamoylamido]pyrrole-2-carboxamido]pyrazole-5-carboxamido]pyrrole-5-carboxamido]propionamidoxime;

3-[1-methyl-3[1-methyl-4 1-methyl-4[3-methyl-4-N,N-bis(2-chloroethyl)aminocinnamoylamido]pyrrole-2-carboxamido]pyrrole-2-carboxamido]pyrazole-5-carboxamido]propionamidoxime;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionitrile;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionitrile;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionitrile;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionitrile;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionitrile;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamide;

3-[1-methyl-3[1-methyl-4[1-methyl-4[4-N-ethyl-N(2-chloroethyl)aminocinnamoylamido]pyrrole-2-carboxamido]pyrrole-2-carboxamido]pyrazole-5-carboxamido]propionamide;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamide;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamide;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propion-N-methyl-amidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propion-N-methyl-amidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propion-N-methyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propion-N-methyl-amidine;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propion-N,N'-dimethyl-amidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propion-N,N'-dimethyl-amidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propion-N,N'-dimethyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamidol propion-N,N'-dimethyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propion-N,N'-dimethyl-amidine;

3-[1-methyl-3[1-methyl-3[1-methyl-4[3-methyl-4-N,N-bis(2-chloroethyl)aminocinnamoylamido]pyrrole-2-carboxamido]pyrazole-5-carboxamido]pyrazole-5-carboxamido]propion-N,N'-dimethyl-amidine;

3-[1-methyl-4[1-methyl-4[1-methyl-4[4-N-ethyl-N(2-chloroethyl)aminocinnamoylamido]pyrrole-2-carboxamido]pyrrole-2-carboxamido]imidazole-2-carboxamido]propion-N,N'-dimethyl-amidine;

2-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]ethylguanidine;

2-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]ethylguanidine;

2-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]ethylguanidine;

2-[1-methyl-3[1-methyl-3[1-methyl-4[3-N,N-bis(2-chloroethyl)aminocinnamoylamido]pyrrole-2-carboxamido]pyrazole-5-carboxamido]pyrazole-5-carboxamido]ethylguanidine.

A further object of the present invention is a process for preparing the compounds of formula (I), and the pharmaceutically acceptable salts thereof, which process comprises:

(a) when B is other than guanidino;

reacting a compound of formula:

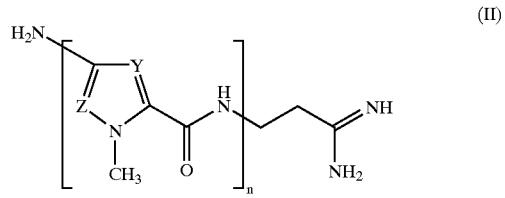

(II)

with a compound of formula:

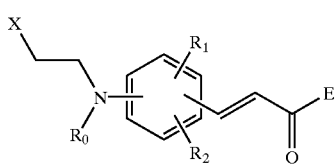
(III)

wherein n, X, $R_0$, $R_1$, $R_2$, Y and Z are as defined above; and E is hydroxy or a suitable leaving group;

so as to obtain a compound of formula:

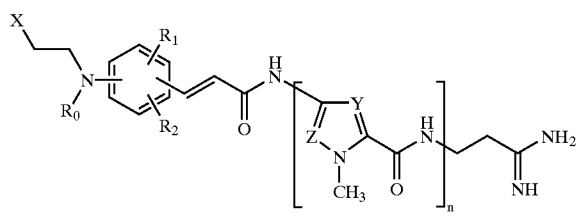
(Ia)

and then, optionally reacting a compound of formula (Ia) with:

(i) $H_2N-(CH_2)_r-NH_2$, wherein r is 2 or 3, so as to obtain a compound of formula (I) having B equal to:

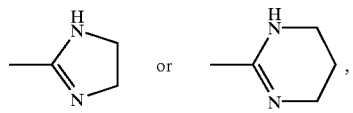

(ii) $H_2N-CN$, so obtaining a compound of formula (I) having B equal to:

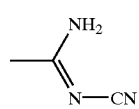

(iii) $H_2N-OH$, so obtaining a compound of formula (I) having B equal to:

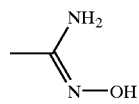

(iv) $HNR_4R_5$, so obtaining a compound of formula (I) having B equal to:

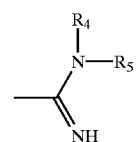

and then optionally with $H_2NR_3$, so obtaining a compound of formula (I) having B equal to:

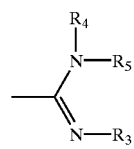

(v) succinic anhydride, so obtaining a compound of formula (I) having B equal to $-\overset{|}{C}=N$;

(vi) water in an alkaline medium, so obtaining a compound of formula (I) having B equal to $-CONR_6R7$ wherein $R_6$ and $R_7$ are both hydrogen atoms;

(vii) $HNR_6R_7$, so obtaining a compound of formula (I) having B equal to:

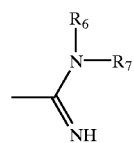

and then with water in an alkaline medium, so obtaining a compound of formula (I) having B equal to $-CONR_6R_7$, wherein $R_6$ and $R_7$ are, each independently, hydrogen or $C_1-C_4$ alkyl; or:

(b) reacting a compound of formula:

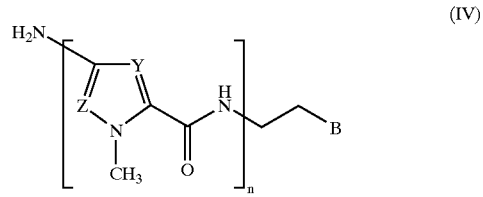
(IV)

with a compound of formula:

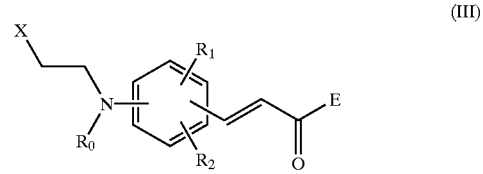
(III)

wherein n, B, Y, Z, X, $R_0$, $R_1$, $R_2$ and E are as defined above;

so obtaining the corresponding compound of formula (I); and, if desired, converting the compound of formula (I) prepared according to processes (a) or (b) into a pharmaceutically acceptable salt thereof.

In formula (III), E is hydroxy or a leaving group selected, for instance, from chloro, 2,4,5-trichlorophenoxy, 2,4-dinitro-phenoxy, succinimido-N-oxy, imidazolyl group, and the like.

The condensation reactions between a compound of formula (II) or of formula (IV) with a compound of formula (III), as defined above according to processes a) or b), can be carried out by known methods, for instance those reported in the aforementioned EP-A-246868.

Likewise, the reaction between a compound of formula (Ia) and one of the reactants as defined under points (i–vii) can be carried out according to known methods, for instance as described in WO 97/43258.

The compounds of formula (II) are known or may be prepared by known methods; see, for a reference, Arcamone et al. in Gazzetta Chim. Ital. 97, 1097 (1967).

Also the compounds of formula (III) and (IV) are known or may be prepared according to well-known reactions in organic chemistry, for instance as reported in WO 97/43258. Salification of a compound of formula (I), as well as preparation of a free compound starting from a salt, may be carried out by known standard methods.

Well known procedures such as, e.g., fractional crystallisation or chromatography, may also be followed for separating a mixture of isomers of formula (I) into the single isomers.

The compounds of formula (I) may be purified by conventional techniques such as, e.g., silica gel or alumina column chromatography, and/or by recrystallisation from an organic solvent such as, e.g., a lower aliphatic alcohol, e.g. methyl, ethyl or isopropyl alcohol, or dimethylformamide.

Pharmacoloay

The compounds of formula (I) according to the present invention are useful as antineoplastic agents.

Particularly, they show cytostatic properties towards tumor cells, so that they can be useful to inhibit growth of various tumors in mammals, including humans, such as, for instance, carcinomas, e.g. mammary carcinoma, lung carcinoma, bladder carcinoma, colon carcinoma, ovary and endometrial tumors. Other neoplasias in which the compounds of the present invention can find application are, for instance, sarcomas, e.g. soft tissue and bone sarcomas, and the hematological malignancies such as, e.g. leukemias.

The in vitro antitumor activity of the compounds of formula (I) was evaluated by cytotoxicity studies carried out on murine L1210 leukemia cells. Cells were derived from in vivo tumors and established in cell culture. The inhibition of cell growth was determined by counting surviving cells with a Coulter Counter after 48 hours treatment.

The in vitro activity was calculated on concentration-response curves and reported as $IC_{50}$ (concentration inhibiting 50% of the cellular growth in respect to controls) were calculated on dose-response.

The compounds of the invention were tested also in vivo on L1210 murine leukemia and on murine reticulosarcoma M 5076, showing a very good antitumoral activity, with the following procedure.

L1210 murine leukemia was maintained in vivo by i.p. weekly transplantation in CD2F1 female mice, obtained from Charles River Italy. For experiments, $10^5$ cells/mouse were injected i.v. in the same strain of mice. Animals were 8 to 10 weeks old at the beginning of the experiments. Compounds were administered i.v. at day +1 after tumor cells injections.

M5076 reticulosarcoma was maintained in vivo by i.m. serial transplantation. For experiments, $5\times10^5$ cells/mice were injected i.m. in the same strain of mice. Animals were 8 to 10 weeks old at the beginning of the experiments. Compounds were administered i.v. at day 3, 7 and 11 after tumor injection.

Survival time of mice and tumor growth were calculated and activity was expressed in term of T/C% and T.I.%.

$$T/C = \frac{\text{median survival time treated group}}{\text{median survival time untreated group}} \times 100$$

T.I. = % inhibition of tumor growth respect to control

Tox=number of mice which died for toxicity.

Tox determination was made when mice died before the control and/or tested significant body weight loss and/or spleen and/or liver size reduction were observed.

The compounds of the invention can be administered to mammals, including humans, through the usual routes, for example, parenterally, e.g. by intravenous injection or infusion, intramuscularly, subcutaneously, topically or orally. The dosage depends on age, weight and conditions of the patient and on the administration route. For example, a suitable dosage for administration to adult humans may range from about 0.1 to about 150–200 mg pro dose 1–4 times a day.

Further object of the present invention are pharmaceutical compositions, which comprise a compound of formula (I) as an active principle, in association with one or more pharmaceutically acceptable carrier and/or diluent. The pharmaceutical compositions of the present invention are usually prepared following conventional methods and are administered in a pharmaceutically suitable form. For instance, solutions for intravenous injection or infusion may contain as a carrier, for example, sterile water or preferably, they may be in the form of sterile aqueous isotonic saline solutions.

Suspensions or solutions for intramuscular injections may is contain, together with the active compound a pharmaceutically acceptable carrier, e.g. sterile water, olive oil, ethyl oleate, glycols, e.g. propylene glycol, and if desired, a suitable amount of lidocaine hydrochloride.

In the forms for topical application, e.g. creams, lotions or pastes for use in dermatological treatment, the active ingredient may be mixed with conventional oleaginous or emulsifying excipients.

The solid oral forms, e.g. tablets and capsules, may contain, together with the active compound, diluents, e.g., lactose, dextrose, saccharose, cellulose, corn starch and potato starch; lubricants, e.g. silica, talc, stearic acid, magnesium or calcium stearate, and/or polyethylene glycols; binding agents, e.g. starches, arabic gums, gelatin, methylcellulose, carboxymethyl cellulose, polyvinylpyrrolidone; disaggregating agents, e.g. starch, alginic acid, alginates, sodium starch glycolate; effervescing mixtures; dyestuffs; sweeteners; wetting agents, for instance, lecithin, polysorbates, laurylsulphates; and, in general, non-toxic and pharmacologically inactive substances used in pharmaceutical formulation. Said pharmaceutical preparations may be manufactured by known techniques, for example by means of mixing, granulating, tabletting, sugar-coating or film-coating processes.

Further object of the present invention are the compounds of formula (I) for use in a method for treating the human or animal body by therapy.

Furthermore, the present invention provides a method for treating tumors in a patient in need of it, which comprises administering to said patient a composition of the invention.

A further object of the present invention is a combined method for treating cancer or for ameliorating the conditions of mammals, including humans, suffering from cancer, said method comprising administering a compound of formula (I), or a pharmaceutically acceptable salt thereof, and an additional antitumor agent, close enough in time and in amounts sufficient to produce a therapeutically useful effect.

The present invention also provides products containing a compound of formula (I), or a pharmaceutically acceptable salt thereof, and an additional antitumour agent as a combined preparation for simultaneous, separate or sequential use in anti-cancer therapy.

The term "antitumor agent" is meant to comprise both a single antitumor drug and "cocktails" i.e. a mixture of such drugs, according to the clinical practice. Examples of antitumor agents that can be formulated with a compound of formula (I), or alternatively, can be administered in a combined method of treatment, include doxorubicin, daunomycin, epirubicin, idarubicin, etoposide, fluorouracil, melphalan, cyclophosphamide, 4-demethoxy daunorubicin, bleomycin, vinblastin, and mitomycin, or mixtures thereof.

The following examples are given to better illustrate the present invention but do not limit the scope of the invention itself.

EXAMPLE 1

3-[1-Methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamidine A solution of 4-N,N'-bis(2-chloroethyl)amino-1-cinnamic acid (200 mg) (prepared as reported in WO 97/43258), dicyclohexylcarbodiimide (162 mg), 1-hydroxybenzotriazole hydrate (106 mg) in DMF (10 ml) was stirred at 70° C. for four hours, cooled to room temperature and then added of 3-[1-methyl-3-[1-methyl-3-[1-methyl-4-aminopyrrole-2-carboxamido]pyrazole-5-carboxamido]pyrazole-5-carboxamido]propionamidine dihydrochloride (310 mg) (prepared as reported in WO 96/05196) and potassium bicarbonate (118 mg).

The mixture was stirred at room temperature for 3 hours, the solvent was evaporated in vacuo and the crude residue purified by flash chromatography (methylene chloride/methanol: 8/2) to yield the title compound as an orange powder (180 mg).

FAB-MS: m/z 725, (100, [M+H]$^+$) PMR (DMSO-$d_6$) d: 11.10 (s, 1H), 10.50 (s, 1H), 10.00 (s, 1H), 8.77 (t, J=5.7 Hz, 1H), 8.79 (b.s., 2H), 8.58 (b.s., 2H), 7.52 (s, 1H), 7.42 (m, 2H), 7.39 (d, J=1.6 Hz, 1H), 7.38 (d, J=15.7 Hz, 1H), 7.29 (s, 1H), 7.01 (d, J=1.6 Hz, 1H), 6.79 (m, 2H), 6.55 (d, J=15.7 Hz, 1H), 4.04 (s, 3H), 4.01 (s, 3H), 3.86 (s, 3H), 3.76 (m, 8H), 3.50 (m, 2H), 2.61 (t, J=6.3 Hz, 2H).

By analogous procedure and using the opportune starting materials the following products can be obtained:

- 3-[1-methyl-3[1-methyl-3[1-methyl-4[4-N-ethyl-N-(2-chloroethyl)aminocinnamoylamido]pyrrole-2-carboxamido]pyrazole-5-carboxamido]pyrazole-5-carboxamido]propionamidine;
- 3-[1-methyl-3[1-methyl-3[1-methyl-4[3-N,N-bis(2-chloroethyl)aminocinnamoylamido]pyrrole-2-carboxamido]pyrazole-5-carboxamido]pyrazole-5-carboxamido]propionamidine;
- 3-[1-methyl-3[1-methyl-3[1-methyl-4[4-N,N-bis(2-chloroethyl)amino-3-methylcinnamoyl]pyrrole-2-carboxamido]pyrazole-5-carboxamido]pyrazole-5-carboxamido]propionamidine;
- 3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionamidine;
- 3-[1-methyl-3[1-methyl-4[1-methyl-4[4-N-ethyl-N(2-chloroethyl)aminocinnamoylamido]pyrrole-2-carboxamido]pyrrole-2-carboxamido]pyrazole-5-carboxamido]propionamidine;
- 3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamidine;
- 3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamidine;
- 3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionamidine;
- 3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propioncyanamidine;
- 3-[1-methyl-4[1-methyl-3[1-methyl-4[4-N,N-bis(2-chloroethyl)aminocinnamoylamido]pyrrole-2-carboxamido]pyrazole-5-carboxamido]propioncyanamidine;
- 3-[1-methyl-4[1-methyl-3[1-methyl-4[4-N,N-bis(2-chloroethyl)aminocinnamoylalmido]pyrrole-2-carboxamido]pyrazole-5-carboxamido]imidazole-2-carboxamido]propionamidoxime;
- 3-1-methyl-3[1-methyl-3[1-methyl-4[4-N-ethyl-N(2-chloroethyl)aminocinnamoylamido]pyrrole-2-carboxamido]pyrazole-5-carboxamido]pyrazole-5-carboxamido]propionamidoxime;
- 3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionitrile;
- 3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxalmido]propionitrile;
- 3-[1-methyl-3[1-methyl-4[1-methyl-4[4-N-ethyl-N(2-chloroethyl)aminocinnamoylamido]pyrrole-2-carboxamido]pyrrole-2-carboxamido]pyrazole-5-carboxamido]propionamide;
- 3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propion-N-methyl-amidine;
- 3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propion-N-methyl-amidine;
- 3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propion-N,N'-dimethyl-amidine;
- 3-[1-methyl-4[1-methyl-4[1-methyl-4[4-N-ethyl-N(2-chloroethyl)aminocinnamoylamido]pyrrole-2-carboxamido]pyrrole-2-carboxamido]imidazole-2-carboxamido]propion-N,N'-dimethyl-amidine;
- 2-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]ethylguanidine.

EXAMPLE 2

3-[1-Methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propion-N,N'-dimethylamidine A solution of 3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5- carboxamido]propionamidine (500 mg) (prepared as reported in example 1) in DMF (20 ml) was heated at 80° C. and treated with methylamine hydrochloride 80% (2 ml). After 4 hours additonal methylamine hydrochloride 80% (2 ml) was added. The solution was evaporated to dryness and the crude residue purified by flash chromatography (methylene chloride/methanol: 8/2) yielding the title compound as a pale yellow powder (300 mg).

FAB-MS: m/z 753, (100,[M+H]$^+$) PMR (DMSO-d$_6$) d: 11.14 (s, 1H), 10.52 (s, 1H), 10.02 (s, 1H), 9.48 (q, J=4.7 Hz, 1H), 8.85 (t, J=5.7 Hz, 1H), 8.73 (q, J=4.7 Hz, 1H), 7.53 (s, 1H), 7.43 (m, 2H), 7.40 (d, J=1.8 Hz, 1H), 7.38 (d, J=15.7 Hz), 7.27 (s, 1H), 7.01 (d, J=1.8 Hz, 1H), 6.79 (m, 2H), 6.55 (d, J=15.7 Hz), 4.03 (s, 3H), 4.00 (s, 3H), 3.86 (s, 3H), 3.75 (m, 8H), 3.50 ((m, 2H), 3.00 (d, J=4.7 Hz, 3H), 2.77 (d, J=4.7 Hz, 3H), 2.74 (t, J=6.6 Hz, 2H).

By analogous procedure and using the opportune starting materials the following products can be obtained:

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamide;

FAB-MS: m/z 726, (100,[M+H]$^+$) PMR (DMSO-d$_6$) d: 11.08 (s, 1H), 10.50 (s, 1H), 9.99 (s, 1H), 8.59 (t, J=5.7 Hz, 1H), 7.52 (s, 1H), 7.43 (m, 2H), 7.39 (d, J=1.9 Hz, 1H), 7.37 (d, J=15.6 Hz), 7.33 (s, 1H), 7.24 (s, 1H), 7.00 (d, J=1.9 Hz, 1H), 6.82 (s, 1H), 6.79 (m, 2H), 6.54 (d, J=15.6 Hz), 4.03 (s, 3H), 4.00 (s, 3H), 3.86 (s, 3H), 3.75 (m, 8H), 3.38 (m, 2H), 2.33 (t, J=7.1 Hz, 2H);

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamidoxime;

FAB-MS: m/z 741, (100, [M+H]$^+$) PMR (DMSO-d$_6$) d: 11.10 (s, 1H), 10.51 (s, 1H), 10.01 (s, 1H), 8.83 (t, J=5.7 Hz, 1H), 8.79 (t, J=5.7 Hz, 1H), 7.53 (s, 1H), 7.43 (m, 2H), 7.40 (d, J=1.8 Hz, 1H), 7.38 (d, J=15.6 Hz), 7.29 (s, 1H), 7.28 (s, 1H), 7.01 (d, J=1.8 Hz, 1H), 6.79 (m, 2H), 6.55 (d, J=15.6 Hz), 4.03 (s, 3H), 4.01 (s, 3H), 3.86 (s, 3H), 3.75 (m, 8H), 3.52 (m, 2H), 2.70 (t, J=6.3 Hz, 1H), 2.58 (t, J=6.3 Hz, 2H);

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propioncyanamidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propioncyanamidine;

3-[1-methyl-4[1-methyl-4[1-methyl-4[4-N-ethyl-N(2-chloroethyl)aminocinnamoylamido]pyrrole-2-carboxamido]pyrrole-2-carboxamido]imidazole-2-carboxamido]propioncyanamidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propioncyanamidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propion-N,N'-dimethyl-amidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propion-N,N'-dimethyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propion-N,N'-dimethyl-amidine;

3-[1-methyl-4[1-methyl-3[1-methyl-4[4-N,N-bis(2-chloroethyl)amino-3-methylcinnamoylamido]pyrrole-2-carboxamido]pyrazole-5-carboxamido]pyrazole-5-carboxamido]propion-N,N'-dimethyl-amidine;

3-[1-methyl-4[1-methyl-4[1-methyl-4[4-N-ethyl-N(2-chloroethyl)aminocinnamoylamido]pyrrole-2-carboxamido]pyrrole-2-carboxamido]imidazole-2-carboxamido]propion-N,N'-dimethyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamide;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propion-N-methyl-amidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propion-N-methyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propion-N-methyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionitrile;

EXAMPLE 3

3-[1-Methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamidine Step I The Intermediate 1-Methyl-4[4-N,N-bis(2-chloroethyl)aminocinnamoylamido]pyrrole-2-carboxylic Acid A solution of 4-N,N'-bis(2-chloroethyl)amino-1-cinnamic acid (100 mg) (prepared as reported in WO 97/43258), dicyclohexylcarbodiimide (80 mg), 1-hydroxybenzotriazole hydrate (50 mg) in DMF (8 ml) was stirred at 70° C. for four hours, cooled to room temperature and then added of 1-methyl-4-aminopyrrole-2-carboxylic acid (70 mg) and potassium bicarbonate (60 mg).

The mixture was stirred at room temperature for 3 hours, the solvent was evaporated in vacuo and the crude residue purified by flash chromatography (methylene chloride/methanol: 9/1) to yield the intermediate compound as a yellow powder (120 mg).

Step II The Title Compound

To a solution of 3[1-methyl-3[1-methyl-3-aminopyrazole-5-carboxamido]pyrazole-5-carboxamido]propionamidine dihidrochloride (prepared as reported in WO 96/05196) (200 mg), intermediate from step I (200 mg), N-(3-dimethylaminopropyl)-N'-ethylcarbodiimide hydrochloride (120 mg), triethylamine (0.15 ml) in DMF (10 ml) was stirred at r.t. overnight. The solvent was evaporated in vacuo and the crude residue purified by flash chromatography (methylene chloride/methanol: 8/2) to yield the title compound as an orange powder (250 mg).

FAB-MS: m/z 750, (30,[M+H]$^+$); 772[100, (M+Na]$^+$)
PMR (DMSO-d$_6$) d: 11.09 (s, 1H), 10.50 (s, 1H), 9.99 (s, 1H), 8.70 (b.s., 2H), 8.20 (b.s., 1H), 7.52 (s, 1H), 7.43 (m, 2H), 7.40 (d, J=1.8 Hz, 1H), 7.38 (d, J=15.6 Hz, 1H), 7.26 (s, 1H), 7.00 (d, J=1.8 Hz, 1H), 6.79 (m, 2H), 6.54 (d, J=15.6 Hz, 1H), 4.02 (s, 3H), 4.00 (s, 3H), 3.86 (s, 3H), 3.75 (m, 8H), 3.50 (b.s., 2H), 2.70 (b.s., 2H);

By analogous procedure and using the opportune starting materials the following products can be obtained:

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamidoxime;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamidoxime;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionamidoxime;

3-[1-methyl-3[1-methyl-3[1-methyl-4[4-N-ethyl-N(2-chloroethyl)aminocinnamoylamido]pyrrole-2-carboxamido]pyrazole-5-carboxamido]pyrazole-5-carboxamido]propionamidoxime;

3-[1-methyl-3[1-methyl-4[1-methyl-4[4-N,N-bis(2-chloroethyl)amino-3-methylcinnamoylamido]pyrrole-2-carboxamido]pyrrole-2-carboxamido]pyrazole-5-carboxamido]propionamidoxime;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionitrile;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionitrile;

3-[1-methy-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamide;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propion-N-methyl-amidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propion-N-methyl-amidine;

2-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]ethylguanidine;

2-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]ethylguanidine;

2-[1-methyl-3[1-methyl-3[1-methyl-4[3-N,N-bis(2-chloroethyl)aminocinnamoylamido]pyrrole-2-carboxamido]pyrazole-5-carboxamido]pyrazole-5-carboxamido]ethylguanidine.

EXAMPLE 4

Tablets each weighing 0.250 g and containing 50 mg of the active substance can be manufactured as follows:

| Composition for 10,000 tablets | |
|---|---|
| 3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionamidine hydrochloride | 500 g |
| Lactose | 1,400 g |
| Corn starch | 500 g |
| Talc powder | 80 g |
| Magnesium stearate | 20 g |

3-[1-methyl-4[1-methyl-4[1-methyl-4[4-N,N-bis(2-chloroethyl)aminocinnamoylamido]pyrrole-2-carboxamido]pyrrole-2-carboxamido]pyrrole-2-carboxamido]propionamidine hydrochloride, lactose and half of the corn starch were mixed; the mixture was then forced through a sieve of 0.5 mm mesh size.

Corn starch (10 g) was suspended in warm water (90 ml) and 5 the resulting paste was used to granulate the powder. The granulate was dried, comminuted on a sieve of 1.4 mm mesh size, then the remaining quantity of starch, talc and magnesium stearate was added, carefully mixed and processed into tablets.

EXAMPLE 5

Capsules, each dosed at 0.200 g and containing 20 mg of the active substance can be prepared as follows:

| Composition for 500 capsules | |
|---|---|
| 3-[1-methyl-3[1-methyl-4[1-methyl-4[4-N,N-bis (2-chloroethyl)aminocinnamoylamido]pyrrole-2-carboxamido]pyrrole-2-carboxamido]pyrazole-5-carboxamido]propionamidine hydrochloride | 10 g |
| Lactose | 80 g |
| Corn starch | 5 g |
| Magnesium stearate | 5 g |

This formulation can be encapsulated in two-piece hard gelatin capsules and dosed at 0.200 g for each capsule.

EXAMPLE 6

Intramuscular Injection 25 mg/ml

An injectable pharmaceutical composition can be manufactured by dissolving 25 g of 3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionamidine hydrochloride in sterile propyleneglycol 1000 ml)and sealing ampoules of 1–5 ml.

We claim:
1. A cinnamoyl distamycin compound of the formula:

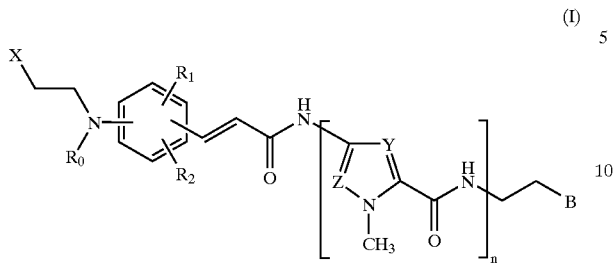

(I)

wherein:

n is 2,3 or 4;

$R_0$ is $C_1$–$C_4$ alkyl or $C_1$–$C_3$ haloalkyl;

$R_1$ and $R_2$, which are the same or different, and are selected from hydrogen, $C_1$–$C_4$ alkyl optionally substituted by one or more fluorine atoms; and $C_1$–$C_4$ alkoxy;

X is a halogen atom;

Y and Z are the same or different, are selected, independently for each heterocyclic ring of the polyheterocyclic chain, from N and CH provided, however, that at least one Y or Z in at least one heterocycle in the compound is N;

B is selected from:

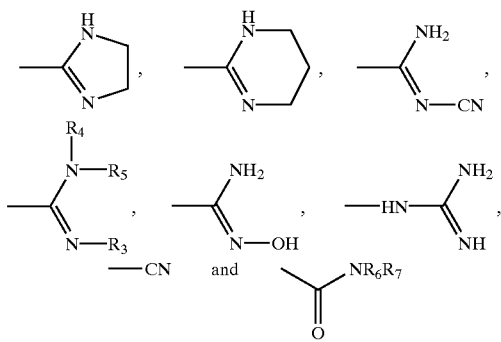

wherein $R_3$, $R_4$, $R_5$, $R_6$, and $R_7$ are, independently from each other, hydrogen or $C_1$–$C_4$ alkyl;

or a pharmaceutically acceptable salt thereof.

2. The compound of claim 1, wherein:

n is 3;

$R_0$ is ethyl or 2-chloroethyl;

$R_1$ and $R_2$, which are the same or different, are selected from hydrogen, methyl, methoxy or trifluoromethyl;

X is chloro;

Y and Z are the same or different, are selected, independently for each heterocyclic ring of the polyheterocyclic chain, from N and CH provided, however, that at least one of Y and Z is N; and B is selected from:

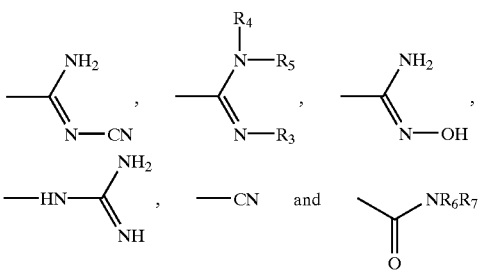

wherein $R_3$, $R_4$, $R_5$, $R_6$, and $R_7$ are, independently from each other, hydrogen or methyl;

or a pharmaceutically acceptable salt thereof.

3. A compound of formula (I) according to claim 1, selected from the group consisting of:

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamidine;

3-[1-methyl-3[1-methyl-3[1-methyl-4[4-N-ethyl-N-(2-chloroethyl)aminocinnamoylamido]pyrrole-2-carboxamido]pyrazole-5-carboxamido]pyrazole-5-carboxamido]propionamidine;

3-[1-methyl-3[1-methyl-3[1-methyl-4[3-N,N-bis(2-chloroethyl)aminocinnamoylamido]pyrrole-2-carboxamido]pyrazole-5-carboxamido]pyrazole-5-carboxamido]propionamidine;

3-[1-methyl-3[1-methyl-3[1-methyl-4[3-methyl-4-N,N-bis(2-chloroethyl)aminocinnamoyl]pyrrole-2-carboxamido]pyrazole-5-carboxamido]pyrazole-5-carboxamido]propionamidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionamidine;

3-[1-methyl-3[1-methyl-4[1-methyl-4[4-N-ethyl-N(2-chloroethyl)aminocinnamoylamido]pyrrole-2-carboxamido]pyrrole-2-carboxamido]pyrazole-5-carboxamido]propionamidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamidine;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionamidine;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propioncyanamidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propioncyanamidine;

3-[1-methyl-4[1-methyl-4[1-methyl-4[4-N,N-bis(2-chloroethyl)aminocinnamoylamido]pyrrole-2- carboxamido]pyrrole-2-carboxamido]imidazole-2-carboxamido]propioncyanamidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propioncyanamidine;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propioncyanamidine;

3-[1-methyl-4[1-methyl-4[1-methyl-4[4-N-ethyl-N(2-chloroethyl)aminocinnamoylamido]pyrrole-2-carboxamido]pyrrole-2-carboxamido]imidazole-2-carboxamido]propioncyanamidine;

3-[1-methyl-4[1-methyl-3[1-methyl-4[4-N-ethylN(2-chloroethyl)aminocinnamoylamido]pyrrole-2-carboxamido]pyrazole-5-carboxamido]imidazole-2-carboxamido]propioncyanamidine;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamidoxime;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionamidoxime;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamidoxime;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamidoxime;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionamidoxime;

3-[1-methyl-3[1-methyl-3[1-methyl-4[4-N-ethyl-N(2-chloroethyl)aminocinnamoylamido]pyrrole-2-carboxamido]pyrazole-5-carboxamido]pyrazole-5-carboxamido]propionamidoxime;

3-[1-methyl-3[1-methyl-4[1-methyl-4[3-methyl-4-N,N-bis(2-chloroethyl)aminocinnamoylamido]pyrrole-2-carboxamido]pyrrole-2-carboxamido]pyrazole-5-carboxamido]propionamidoxime;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionitrile;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propionitrile;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionitrile;

3-[1-methyl-4[1-methyl-4[1-methyl-4[4-N,N-bis(2-chloroethyl)aminocinnamoylamido]pyrrole-2-carboxamido]pyrazole-5-carboxamido]imidazole-2-carboxamido]propionitrile;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propionitrile;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propionamide;

3-[1-methyl-3[1-methyl-4[1-methyl-4[4-N-ethyl-N(2-chloroethyl)aminocinnamoylamiido]pyrrole-2-carboxamido]pyrrole-2-carboxamidozpyrazole-5-carboxamido]propionamide;

3[-1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propionamide;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propionamide;

3-1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propion-N-methyl-amidine;

3-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]propion-N-methyl-amidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propion-N-methyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propion-N-methyl-amidine;

3-[1-methyl-3[1-methyl-3[1-methyl-4[4-N,N-bis(2-chloroethyl)aminocinnamoylamido]pyrrole-2-carboxamido]pyrazole-5-carboxamido]pyrazole-5-carboxamido]propion-N,N'-dimethyl-amidine;

3-[1-methyl -3[1-methyl -4[1-methyl -4[4-N,N-bis(2-chloroethyl)aminocinnamoylamido]pyrrole-2-carboxamido]pyrrole-2-carboxamido]pyrazole-5-carboxamido]propion-N,N'-dimethyl-amidine;

3-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]propion-N,N'-dimethyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]imidazole-2-carboxamido]propion-N,N'-dimethyl-amidine;

3-[1-methyl-4[1-methyl-3[1-methyl-4[4-N,N-bis(2-chloroethyl)aminocinnamoylamido]pyrrole-2-carboxamido]pyrazole-5-carboxamido]pyrrole-2-carboxamido]propion-N,N'-dimethyl-amidine;

3-[1-methyl-3[1-methyl-3[1-methyl-4[3-methyl-4-N,N-bis(2-chloroethyl)aminocinnamoylamido]pyrrole-2-carboxamido]pyrazole-5-carboxamido]pyrazole-5-carboxamido]propion-N,N'-dimethyl-amidine;

3-[1-methyl-4[1-methyl-4[1-methyl-4[4-N-ethyl-N(2-chloroethyl)aminocinnamoylamido]pyrrole-2-carboxamido]pyrrole-2-carboxamido]imidazole-2-carboxamido]propion-N,N'-dimethyl-amidine;

2-[1-methyl-3[1-methyl-3[1-methyl-4[4-N,N-bis(2-chloroethyl)aminocinnamoylamido]pyrrole-2- carboxamido]pyrazole-5-carboxamido]pyrazole-5-carboxamido]ethylguanidine;

2-[1-methyl-3[1-methyl-4[1-methyl-4[4-N,N-bis(2-chloroethyl)aminocinnamoylamido]pyrrole-2-carboxamido]pyrrole-2-carboxamido]pyrazole-5-carboxamido]ethylguanidine;

2-[1-methyl-4[1-methyl-4[1-methyl-4[4-N,N-bis(2-chloroethyl)aminocinnamoylamido]pyrrole-2-carboxamido]pyrrole-2-carboxamido]imidazole-2-carboxamido]ethylguanidine;

2-[1-methyl-3[1-methyl-3[1-methyl-4[3-N,N-bis(2-chloroethyl)aminocinnamoylamido]pyrrole-2-carboxamido]pyrazole-5-carboxamido]pyrazole-5-carboxamido]ethylguanidine; and the pharmaceutically acceptable salts thereof.

4. A composition comprising a compound according to claim 1 as an active principle in an amount effective to inhibit growth of tumor cells, in association with one or more pharmaceutically acceptable carriers and/or diluents.

5. A composition comprising:
a compound of claim 1, and a pharmaceutically acceptable carrier therefor, wherein the composition inhibits the growth and proliferation of tumor cells when administered in vivo to a patient in an amount effective to inhibit the growth and proliferation.

6. A method for preparing a compound of formula (Ia), the method comprising:
reacting a compound of formula:

(II)

with a compound of formula:

(III)

wherein E is hydroxy or a suitable leaving group;
n is 2, 3 or 4;
$R_0$ is $C_1$–$C_4$ alkyl or $C_1$–$C_3$ haloalkyl;
$R_1$ and $R_2$, which are the same or different, and are selected from hydrogen, $C_1$–$C_4$ alkyl optionally substituted by one or more fluorine atoms; and $C_1$–$C_4$ alkoxy;
X is a halogen atom;
Y and Z are the same or different, are selected, independently for each heterocyclic ring of the polyheterocyclic chain, from N and CH provided, however, that at least one of Y and Z is N;
under conditions and a time effective to obtain a compound of formula Ia (Ia)

and isolating the compound of formula Ia.

7. A method according to claim 6 wherein, within the compounds of formula (III), E is a leaving group selected from the group consisting of chloro, 2,4,5-trichlorophenoxy, 2,4-dinitro-phenoxy, succinimido-N-oxy and imidazolyl.

8. The method of claim 6, wherein the time is about 1 hour to about 24 hours and the conditions are in the range of −10° C. to 50° C.

9. A method of preparing a compound of formula (I), (I)

wherein:

n is 2, 3 or 4;
$R_0$ is $C_1$–$C_4$ alkyl or $C_1$–$C_3$ haloalkyl;
$R_1$ and $R_2$, which are the same or different, and are selected from hydrogen, $C_1$–$C_4$ alkyl optionally substituted by one or more fluorine atoms; and $C_1$–$C_4$ alkoxy;
X is a halogen atom;
Y and Z are the same or different, are selected, independently for each heterocyclic ring of the polyheterocyclic chain, from N and CH provided, however, that at least one of Y and Z is N;
B is selected from:

wherein $R_3$, $R_4$, $R_5$, $R_6$, and $R_7$ are, independently from each other, hydrogen or $C_1$–$C_4$ alkyl;

or a pharmaceutically acceptable salt thereof; wherein said method comprises:

reacting a compound of formula:

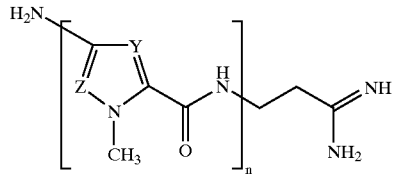
(II)

with a compound of formula:

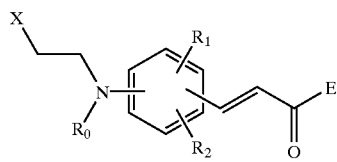
(III)

wherein E is hydroxy or a suitable leaving group;

n is 2, 3 or 4;

$R_0$ is $C_1$–$C_4$ alkyl or $C_1$–$C_3$ haloalkyl;

$R_1$ and $R_2$, which are the same or different, and are selected from hydrogen, $C_1$–$C_4$ alkyl optionally substituted by one or more fluorine atoms; and $C_1$–$C_4$ alkoxy;

X is a halogen atom;

Y and Z are the same or different, are selected, independently for each heterocyclic ring of the polyheterocyclic chain, from N and CH provided, however, that at least one of Y and Z is N;

under conditions and a time effective to obtain a compound of formula (Ia); thereby obtaining a compound of formula:

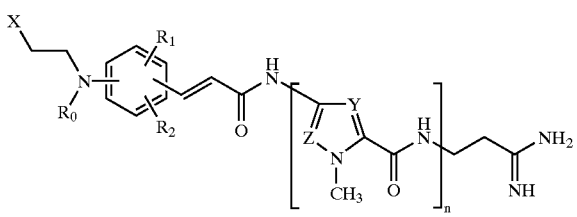
(Ia)

and isolating the compound of formula (Ia), and reacting the compound of formula (Ia) with a reactant selected from the group consisting of (a) $H_2N$—$(CH_2)_r$—$NH_2$, (b) $H_2N$—CN, (c) $H_2N$—OH, (d) $HNR_4R_5$, (e) $HNR_4R_5$ followed by $H_2NR_3$, (f) water in an alkaline medium, (g) $HNR_6R_7$, or (h) $HNR_6R_7$ followed by water in an alkaline medium, under conditions and a time effective to obtain a compound of formula (I), and isolating the compound of formula (I).

10. The method of claim 9, wherein the time is about 2 hours to about 48 hours and the conditions are in the range of about 0° C. to 100° C.

11. A method for preparing a cinnamoyl distamycin compound of the formula (I) as claimed in claim 1, the method comprising:

reacting a compound of formula:

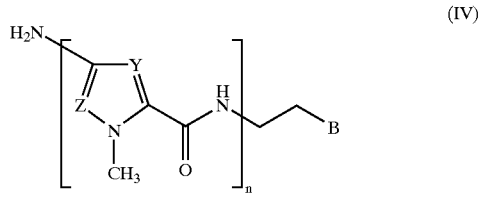
(IV)

with a compound of formula:

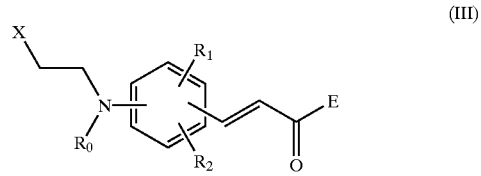
(III)

wherein n, B, Y, Z, X, $R_0$, $R_1$, $R_2$ and E are as defined above, wherein said reacting is carried out for a time and under conditions effective to form the compound of formula (I), and isolating the compound of formula (I), and optionally converting the compound of formula (I) into a salt.

12. The method of claim 11, wherein the time is about 2 hours to about 48 hours and the conditions are in the range of about 0° C. to 100° C.

13. A method of inhibiting growth of tumor cells, comprising:

exposing tumor cells to a compound of claim 1 for a time and under conditions effective to inhibit the growth of the tumor cells.

14. A method of inhibiting growth of tumor cells comprising administering to the patient in need thereof a compound according to claim 1 for a time and under conditions effective to inhibit growth of said tumor cells.

* * * * *